United States Patent [19]
Fischer et al.

[11] Patent Number: 5,265,638
[45] Date of Patent: Nov. 30, 1993

[54] MAGNETO-PNEUMATIC INTERMITTENT SUCTION DEVICE

[75] Inventors: Russell J. Fischer, North Plainfield; Ronald L. Tobia, Tinton Falls, both of N.J.; Michael D. Leshner, Columbia, Md.

[73] Assignee: BOC Health Care, Inc., Liberty Corner, N.J.

[21] Appl. No.: 995,391

[22] Filed: Dec. 22, 1992

[51] Int. Cl.⁵ .................................. G05D 16/06
[52] U.S. Cl. .................. 137/103; 137/624.14; 251/65; 604/120
[58] Field of Search .......... 137/103, 105, 624.14; 251/65; 604/120, 317

[56] References Cited

U.S. PATENT DOCUMENTS

| | | |
|---|---|---|
| 2,292,401 | 8/1942 | Orre ................... 137/103 |
| 2,652,847 | 9/1953 | Segebarth ............ 137/103 |
| 2,669,249 | 2/1954 | Wittmann ........... 251/65 X |
| 2,991,805 | 7/1961 | Page ..................... 251/65 X |
| 3,216,328 | 11/1965 | Peterson ............ 137/624.14 X |
| 3,659,605 | 5/1972 | Sielaff . |
| 3,812,855 | 5/1974 | Banko . |
| 4,303,072 | 12/1981 | Lewis . |
| 4,315,506 | 2/1982 | Kayser et al. . |
| 4,600,034 | 7/1986 | Ko . |
| 4,635,681 | 1/1987 | Boldish . |
| 4,747,577 | 5/1988 | Dimock . |
| 4,750,705 | 6/1988 | Zippe . |
| 4,767,403 | 8/1988 | Hodge . |
| 4,782,849 | 11/1988 | Hodge ................... 137/103 |
| 4,819,693 | 4/1989 | Rodder . |

FOREIGN PATENT DOCUMENTS 970912   9/1964   United Kingdom .

Primary Examiner—Robert G. Nilson
Attorney, Agent, or Firm—Roger M. Rathbun; Larry R. Cassett

[57] ABSTRACT

An intermittent suction device for removing fluids from a patient where the duty cycle between the OFF and ON cycles is controlled by a magnetically susceptible diaphragm that switches back and forth between first and second positions, representing ON and OFF positions, by controlling the differential pressure across the diaphragm. The diaphragm is biased toward it first position by a permanent magnet that acts to attract the flexible diaphragm. The device has few moving parts and its duty cycle and overall cycle times are easily adjusted by the user.

24 Claims, 3 Drawing Sheets

MAGNETO-PNEUMATIC INTERMITTENT SUCTION DEVICE

BACKGROUND OF THE INVENTION

This invention relates to an in intermittent suction device for removing fluids from body cavities of a patient, and, more particularly, to a means of providing timed sequence of vacuum/nonvacuum to that patient for such fluid removal.

Intermittent suction devices are routinely used in medical environments, such as hospital recovery rooms where such devices are continually affixed to the patient and which are employed post-operatively to drain patient cavities, such as the stomach.

Typical of such devices are as shown in U.S. Pat. No. 3,359,605 of Sielaff. In the Sielaff device, an intermittent timed cycle is used to alternate between two states; one where the vacuum is actually being applied to the patient cavity, and the other where the vacuum is terminated and and atmospheric pressure is applied to the patient cavity in order that fluids in the withdrawal tubing may briefly flow backwardly toward the patient to clear the lines.

Further, normally such devices have the ability to operate off of normal piped vacuum available in operating room, recovery rooms and the like in hospitals.

While the Sielaff device is a reliable, widely used device, it is advantageous to provide an improved device having the least complexity without sacrificing reliability, such that the device has a minimum of moving parts, few parts to wear and yet which achieves greater reliability and operating lifetime. In addition, since current such devices are relatively inexpensive, any new device preferably needs to be easy to manufacture at a low cost.

BRIEF SUMMARY OF THE INVENTION

The present intermittent device thus is powered by line vacuum available in hospital environments and which employs very few moving parts. The very simplicity of the device provides reduced manufacturing costs over the Sielaff device and requires less servicing by virtue of the simple mechanical assembly such that disassembly and cleaning is relatively simple, wear is minimized by the presence of but two moving parts, while reliability is enhanced. Also, due to the simplified design, relatively large ports can be used, thus eliminating the need for microfine filters to trap particles that could clog small ports.

The device includes a unique arrangement where control of the timed vacuum/atmospheric pressure cycles to the patient are controlled by a flexible diaphragm that divides a chamber into two subchambers. The flexible diaphragm is susceptible to magnetic forces, that is, the flexible diaphragm may itself contain a permanent magnet or alternatively, can be produced by using a magnetically polarized diaphragm material.

One of the subchambers includes an inlet that is connectible to the source of vacuum and an outlet that is connectible to the tube or device that goes to the patient cavity. The flexible diaphragm is magnetically biased to one of two positions. In the preferred embodiment, the diaphragm is magnetically biased toward a first position where the inlet and outlet are in communication with each other such that the vacuum available at the inlet is administered through the outlet to the patient. By controlling the differential pressure between the two subchambers, that is, across the flexible diaphragm, a pressure differential can be reached that overcomes the magnetic bias sufficiently to move the diaphragm to its second position where communication between the inlet and the outlet is blocked, thereby cutting off the vacuum to the patient.

Thus, in the design of the present device, a reliable switching valve may be constructed by designing the amount of magnetic bias on the flexible diaphragm and by providing a change in the differential pressure between the subchambers to be of a predetermined threshold amount to move the diaphragm from its biased position to its other position.

As a further feature of the present invention, the timing means that controls the changes in differential pressure in the aforementioned subchambers to move the diaphragm is also constructed through the use of a chamber having a magnetically attractable diaphragm and which itself moves between two positions based upon the relative differential pressure between its subchambers. In the preferred embodiment, both diaphragms are built into a common housing and the magnetic bias provided to both of the diaphragms is from a common source such as a permanent magnet located intermediate the two flexible diaphragms.

As will also be seen, the timing means may be used for other purposes than control as an intermittent suction device for removing fluids from a patient and such other uses are described in Applicant's copending patent application.

BRIEF DESCRIPTION OF THE DRAWING

The above and other features and embodiments of this invention will become still further apparent from a consideration of the following description and accompanying drawings which show the preferred embodiment of the invention on which.

DESCRIPTION OF THE PREFERRED EMBODIMENT

Figure 1:
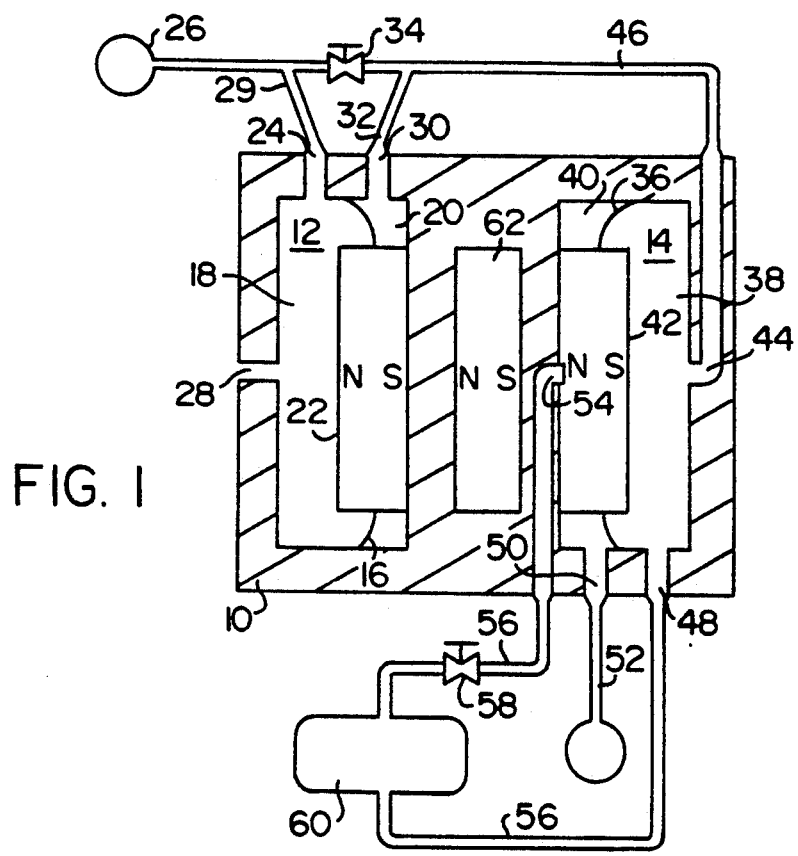
FIG. 1 is a schematic view of the present invention in its initial position before a source of vacuum has been activated.

Referring now to FIG. 1, there is shown a schematic view of an intermittent suction device for a patient constructed in accordance with the present invention. A housing 10 is provided and within which there are formed a first chamber 12 and a second chamber 14. Taking initially, the first chamber 12, a flexible diaphragm 16 is sealed within the interior of first chamber 12 and separates first chamber 12 into first and second subchambers 18, 20 respectively.

Flexible diaphragm 16 is manufactured such that it is susceptible to magnetic forces and thus is attracted and/or repelled by a magnetic force. In the embodiment shown, a permanent magnet 22 is affixed to a non-magnetic diaphragm, or, as a alternate, the flexible diaphragm 16 itself could by manufactured by using a magnetically polarized diaphragm material. In either case, or in the case of some other alternate, the important property required in the diaphragm is that it be magnetically susceptible to magnetic forces having polarity, that is, a north and south magnetic orientation.

An inlet 24 is formed in first subchamber 18 of first chamber 12 and is connectible to a source of vacuum 26 by means such as tubing 29. The vacuum source 26 may be the normal regulated vacuum found in various locations in hospitals. The vacuum is commonly piped to rooms including operating and recovery rooms from a central vacuum pumping system located a a central location in the hospital. The vacuum of such hospital systems typically may range within 300-600 mm Hg.

An outlet 28 is also formed in the first subchamber 18 of first chamber 12 and is connectible to some means of communicating the vacuum to the particular patient cavity that is being drained of fluids. Such devices are well known and include sump tubes that are placed within the patient and connected to an intermittent suction device by flexible tubing.

There is also an opening 30 formed in the second subchamber 20 of first chamber 12 and which is also connectible to the vacuum source 26 through suitable tubing 32, however, a variable restrictor 34 is located in the communication path between opening 30 and the source of vacuum 26, for reasons that will be later explained. As will be apparent, the preferred embodiment will be described as including variable restrictors, however, fixed restrictors may be used with an intermittent suction device where the duty cycle is fixed and changes in the cycle are not required to be easily made by the user.

Figure 2:
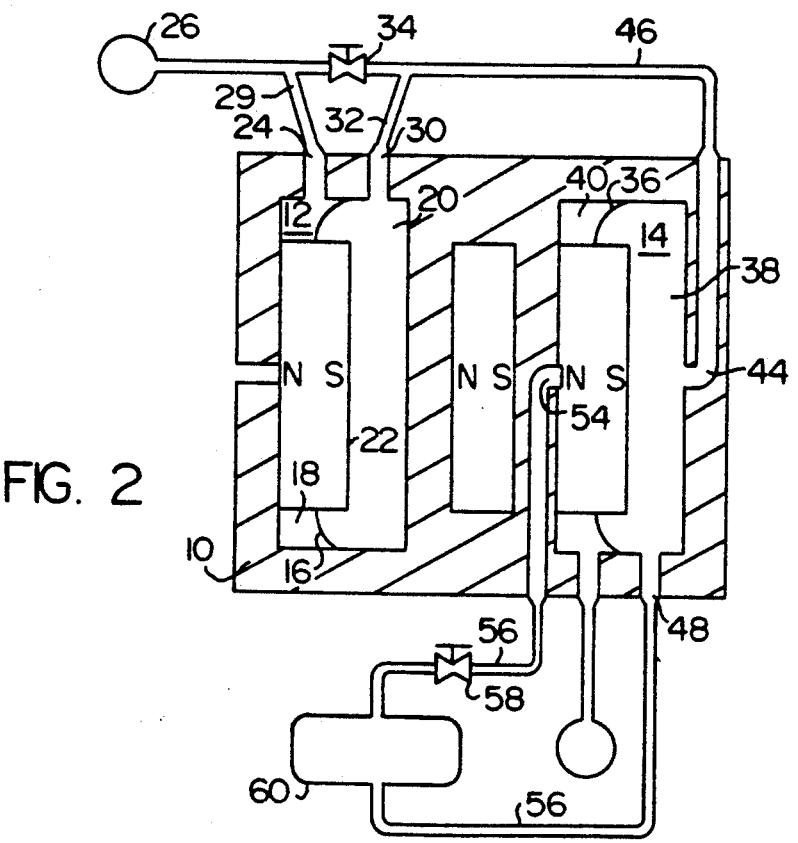
FIG. 2 is a schematic view of the present invention in its OFF portion of its duty cycle where vacuum is not being supplied to the patient.
Figure 3:
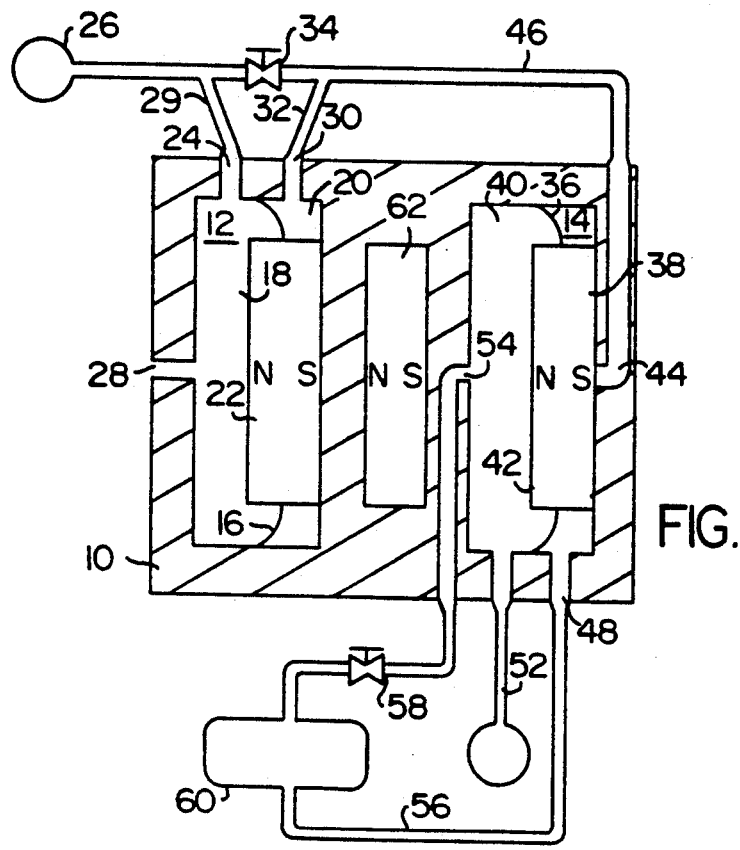
FIG. 3 is a further schematic view of the invention during its ON portion of its duty cycle and atmospheric pressure is being applied to the patient.

The flexible diaphragm 16 of the first chamber 12 is movable between two positions, a first position as shown in FIGS. 1 & 3 and a second position as shown in FIG. 2 and again the movement with respect to the two positions will be explained in connection with the operation of the device.

The second chamber 14 also contains a flexible diaphragm 36 and which separates the second chamber 14 into first and second subchambers 38,40 respectively. Again, the flexible diaphragm of the second chamber is constructed similar to the flexible diaphragm 16 of the first chamber 12 and, in the preferred embodiment, contains a permanent magnet 42.

A vacuum port 44 is formed in the first subchamber 38 of second chamber 14 and is connectible to the vacuum source 26 by means of suitable tubing 46 and again, the path formed between first subchamber 38 and vacuum source 26 includes a variable restrictor 34. A bypass opening 48 is also formed in the first subchamber 38 and its purpose later explained. Throughout the explanation of the present invention, for convenience, the fluid pathways may be referred to as tubings, however, such pathways could readily be formed in the housing itself in a molded plastic material.

In the second subchamber 40 of second chamber 14, there is formed a atmospheric pressure opening 50 and which leads via suitable tubing 52 to ambient atmosphere. A bypass port 54 formed in second subchamber 40 of second chamber 14 communicates by means of tubing 56 to the bypass opening 48 and thus into the first subchamber 38 of second chamber 14. In the tubing 56, however, there is also present a variable restrictor 58 and a compliance chamber 60. Again, the variable restrictor 58 could be fixed.

The flexible diaphragm 36 in second chamber 14 is moveable between two positions, the first of those positions is depicted in FIGS. 1 & 2 and the second of those positions is depicted in FIG. 3.

Finally, a permanent magnet 62 is positioned intermediate the permanent magnets 22, 42 within flexible diaphragms 16, 36 and which creates a magnetic attraction or bias on those diaphragms. The polarity of the various magnets and/or magnetic diaphragms is such that permanent magnet 62 has an opposite pole facing the pole of the diaphragm permanent magnets 22, 42 such that those flexible diaphragms 16, 36 are magnetically biased to their first positions as shown in FIG. 1.

Having described the overall structure of the intermittent suction device of the present invention, a summary of its operation will now be presented with reference to FIGS. 1-3.

Initially the intermittent suction device is as shown in FIG. 1 prior to the activation of supply vacuum. As explained, the magnetic bias exerted by the permanent magnet 62 on the magnetic force susceptible flexible diaphragms 16,36 retain those diaphragms 16,36 in their first positions as shown in FIG. 1. When the vacuum source 26 is activated, a pressure drop is immediately developed across the variable resistor 34. Vacuum from vacuum source 26 is immediately applied to the first subchamber 18 of first chamber 12.

That relatively lower pressure in the first subchamber 18 causes a predetermined pressure differential between the that lower pressure in the first subchamber 18 and the pressure within the second subchamber 20. As noted, even though the second subchamber 20 is connected to the same vacuum source 26 as the first subchamber 18, the variable flow restrictor 34 creates a pressure differential.

The magnitude of the pressure differential between first and second subchambers 18, 20 is designed to be sufficient to overcome the magnetic bias exerted on permanent magnet 22 sealed to flexible diaphragm 16 causing that flexible diaphragm 16 to rapidly switch from its first to it's second position as shown in FIG. 2 where flexible diaphragm 16 seals outlet 28 thus preventing vacuum from vacuum source 26 from reaching the patient. The intermittent suction device is thus in its "OFF" position and fluids are not being withdrawn from the patient.

Simultaneously, the vacuum from vacuum source 26 is being applied to the compliance chamber 60 through variable restrictor 34 through open vacuum port 44. (FIG. 1). The pressure in the compliance chamber 60 thus begins to decrease at a rate that is determined by the value of the resistance set at variable restrictor 34 and by the capacity or volume of the compliance chamber 60. As will become apparent, the rate of decrease of pressure within compliance chamber 60 is determinative of the "OFF" cycle, that is, the time that the intermittent suction device remains in the "OFF" status of its duty cycle. The duration of that cycle is therefore set or adjusted as desired by changing the value of the resistance at variable restrictor 34.

Eventually, the pressure drops sufficiently within first subchamber 38 of second chamber 14 to create a sufficient pressure differential between the first subchamber 38 and the second subchamber 40 of second chamber 14 that the magnetic bias exerted on flexible diaphragm 36 by permanent magnet 62 is overcome and the flexible diaphragm 36 moves from its first position as shown in FIG. 2 to its second position as shown in FIG. 3 where it seals against vacuum port 44, thereby closing off the source of vacuum to second chamber 14 and thus to compliance chamber 60.

Since the vacuum port 44 is now closed and compliance chamber disconnected from tubing 46, the pressure in the tubing 46 and at opening 30 into the second subchamber 20 of first chamber 12 rapidly drops to full vacuum from the vacuum source 26, thus the differential pressure between first and second subchambers 18, 20 of first chamber 12 is reduced to the point that the magnetic bias exerted by the permanent magnet 62 on permanent magnet 22 of flexible diaphragm 16 moves flexible diaphragm 16 back to its first position as shown in FIG. 3. When flexible diaphragm 16 thus returns to its first position, the outlet 28 is opened and the vacuum from vacuum source 26 passes through first subchamber 18 of first chamber 12 to be applied to the patient cavity for withdrawal of fluids thus initiating the "ON" cycle of the intermittent suction device.

As the "ON" cycle continues (FIG. 3). the compliance chamber 60 is being vented to atmosphere through bypass port 54 and variable restrictor 58. The pressure within compliance chamber 60 therefore increases at a rate determined as a function of the resistance set at variable restrictor 58 and the capacity of compliance chamber 60. Again, as with the "OFF" cycle, the variable restrictor 58 is adjustable to enable the operator to choose a value desired and that selection determines the duration of the "ON" cycle.

The "ON" cycle thus continues until the pressure in the compliance chamber 60 has increased such that the differential pressure across flexible diaphragm 36 is reduced to a threshold value and the magnetic bias exerted on flexible diaphragm 36 by permanent magnet 62 causes flexible diaphragm 36 to move back to its first position as shown in FIG. 1. At this point, the intermittent suction device has completed a full cycle and is back to its status as shown in FIG. I and the cycling continues as described.

Thus the device cycles through the use of a pair of magnetically biased, flexible diaphragms and through the control and timing of the differential pressures exerted across the flexible diaphragms operating in conjunction with that magnetic bias exerted on such flexible diaphragm.

Figure 4:
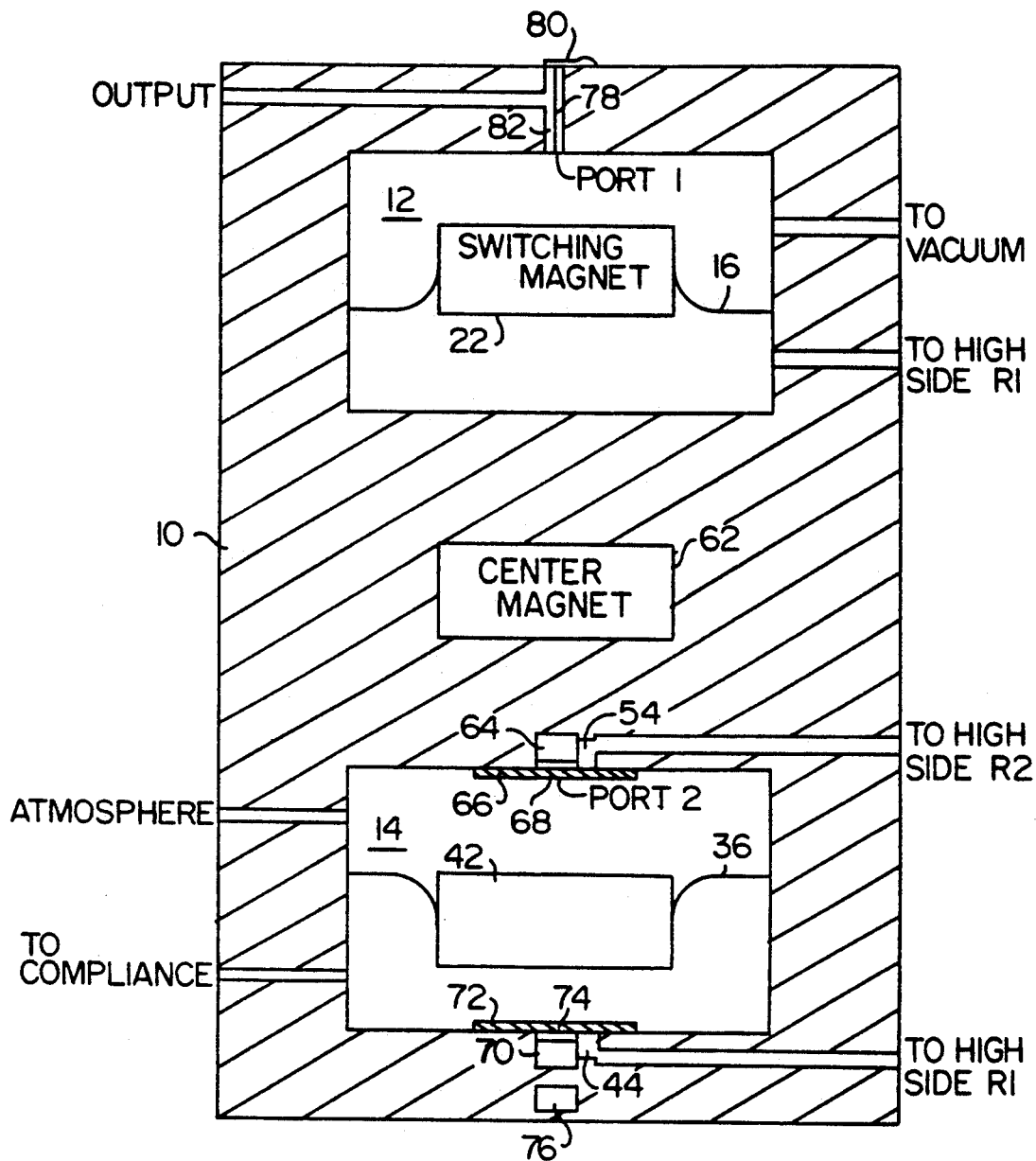
FIG. 4 is a schematic view of a further embodiment of the present invention including certain magnetic valves.

Turning now to FIG. 4, there is shown a schematic of a further embodiment of the intermittent suction device of the present invention and where like numbers have been used for corresponding parts and features of the FIGS. 1-3 embodiment.

In this embodiment, additional features have been added to enhance the operation of the device in carrying out the removal of fluids from a patient. In particular, it is extremely important that the bypass port 54 and the vacuum port 44 of the second chamber 14 be completely and fully sealed when the flexible diaphragm 36 is in its first and second positions since any leakage through the closed ports can cause a significant effect on the timing cycles, i.e. the duty cycle, or times during which the unit is in its "ON" cycle and its "OFF" cycle.

Accordingly, the FIG. 4 embodiment creates a better seal between the flexible diaphragm 36 and the respective bypass port 54 and vacuum port 44 when flexible diaphragm 36 is in its first and second positions.

In the bypass port 54 of the second chamber 14, a seal magnet 64 is positioned in the bypass port 54 and a compliant seat 66 is sealed over bypass port 54 having a small opening 68 in compliant seat 66. The compliant seat 66 is manufactured out of a flexible material such as thin latex having a thickness of about 0.030 inches and is sealed around bypass port 54. When flexible diaphragm 36 is attracted by permanent magnet 62 to its first position, seal magnet 64 is attracted by the permanent magnet 42 in flexible diaphragm 36 and small opening 68 is thus closed by being sandwiched between permanent magnet 42 and seal magnet 64, thus insuring a good leakproof seal for bypass port 54.

As is understood, the polarity of seal magnet 64 must be arranged such that its pole facing the permanent magnet 42 of flexible diaphragm 36 is opposite that of the permanent magnet 42 so that there is an attraction between the two magnets. The magnetic attractive force of seal magnet 64, although not trivial, can effectively be ignored when dealing with the equations with respect to the magnetic attraction of the permanent magnet 62 on permanent magnets 22 and 42. Thus, the timing of the "ON" and "OFF" duty cycles are unaffected by the addition of the seal magnet 64.

When, in accordance with the description of the operation of the device, flexible diaphragm 36 moves to its second position opening bypass port 54 and closing vacuum port 44, the attractive forces between permanent magnet 42 and seal magnet 64 will be reduced and the seal magnet 64 will be drawn to its position shown in FIG. 4 away from compliant seat 66 by the attractive force of the permanent magnet 62. Thus vacuum port 44 becomes fully opened.

A similar type of seal is found at the vacuum port 44 where a seal magnet 70 is provided within the vacuum port 44 and which is attracted by permanent magnet 42 to sandwich compliant seat 72 between the permanent magnet 42 and seal magnet 70 to close small opening 74 in compliant seat 72.

In addition, however, a negative bias magnet 76 is also included within housing 10 and is located adjacent seal magnet 70 with opposite poles of the seal magnet 70 and negative bias magnet 76 facing each other. The negative bias magnet 76 serves to attract the seal magnet 70 away from compliant seat 72 when permanent magnet 42 and diaphragm 36 are in the first position and the attraction of permanent magnet 42 no longer influences seal magnet 70, and small opening 74 is thus uncovered.

As a further feature of the FIG. 4 embodiment, an atmospheric vent 78 provides the means of venting the patient cavity when vacuum is no longer being applied to the patient. There are obviously many ways of providing such venting, however, in the FIG. 4 embodiment, the vent 78 is incorporated into the same housing 10 as the other operative elements of the intermittent suction device. A flexible flapper 80 biased toward the closed position covering atmospheric vent 78 is moved to its open position by means such as a stem 82. Stem 83 has its end 84 projecting a predetermined distance downwardly into first chamber 12. As the permanent magnet 22 within flexible diaphragm moves to its second position, the permanent magnet 22 engages the end 84 of stem 82 and moves it sufficiently to open flexible flapper 80 to provide an atmospheric vent to the line leading to the patient (not shown in FIG. 4). In this way, as in the Sielaff patent, whenever the vacuum is interrupted to the patient, that is, the intermittent suction device is in its "OFF" position, the patient line is automatically opened to atmospheric pressure.

Figure 5:
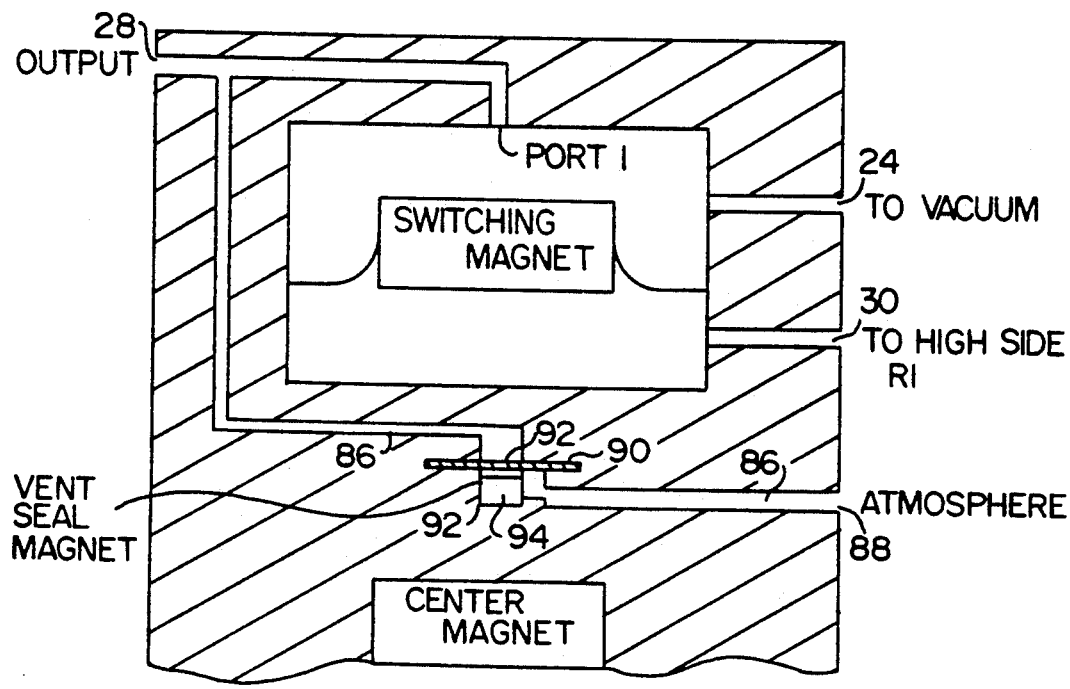
FIG. 5 is a partial schematic view of a further embodiment of the present invention having a magnetic atmospheric vent valve.

Turning lastly to FIG. 5, a still further means of effecting the venting of the line leading to the patient is shown by means of magnetic valves. In this embodiment, a vent conduit 86 is formed in housing 10 between the outlet 28 and an opening 88 to atmosphere.

A magnetic valve means is provided in the vent conduit 86 comprising a compliant seat 90 that crosses vent conduit 86 and has an opening 92 formed therein.

A vent seal magnet 94 is located adjacent compliant seat 90 and is acted upon by permanent magnet 62 and, at times, by permanent magnet 22 in flexible diaphragm 16.

When, therefore, diaphragm 16 is in its first position, that is, away from outlet 28, (vacuum is being administered to the patient), the polarity is such that permanent magnet 22 within diaphragm 16 attracts the vent seal magnet 94 and causes it to position itself tightly against the compliant seat 90 thereby closing vent opening 92.

When, on the other hand, the flexible diaphragm 16 is in its second position ("OFF" position), the magnetic attraction between permanent magnet 22 and vent seal magnet 94 is lost and vent seal magnet 94 is instead, attracted by permanent 62 and is pulled away from compliant seat 90, thus opening the opening 92 to allow atmospheric pressure to enter the vent conduit 86 all the way to the outlet 28 where it is applied to the patient as described in the aforesaid Sielaff patent to release materials that may be obstructing the pathway from the patient.

While the invention has been disclosed and described with reference to a single embodiment, it will be apparent that variations and modifications may be made therein, and it is therefore intended in the following claims to cover each such variation and modification as falls within the true spirit and scope of the invention.

We claim:

1. An intermittent suction device for supplying a timed vacuum to a patient from a vacuum source for removing fluids from the patient, said device comprising a housing having a chamber, said chamber having a flexible diaphragm separating said chamber into first and a second subchambers, said first subchamber having an inlet adapted to be connected to the source of vacuum and an outlet for applying vacuum from the source to the patient, said flexible diaphragm having a first position wherein said outlet is open to communicate vacuum from said vacuum source to said outlet and a second position wherein said flexible diaphragm closes said outlet to prevent communication of vacuum between said inlet and said outlet, said diaphragm being susceptible to magnetic forces, magnetic force means biasing said flexible diaphragm to said first position and control means to control the differential pressure between said first and second subchambers to move said diaphragm between said first and second positions at predetermined time intervals.

2. An intermittent suction device as described in claim 1 wherein said flexible diaphragm includes a permanent magnet.

3. An intermittent suction device as described in claim 2 wherein said diaphragm opens said outlet by the force of said permanent magnet acting on a magnetic valve.

4. An intermittent suction device as described in claim 1 wherein said flexible diaphragm is comprised of a magnetically polarized material.

5. An intermittent suction device as described in claim 1 wherein said control means comprises means to create a positive pressure differential between said second subchamber and said first subchamber in an amount sufficient to overcome the magnetic force biasing said flexible diaphragm to cause said flexible diaphragm to move from said first to said second position.

6. An intermittent suction device as described in claim 5 wherein said control means comprises means to cause the pressure differential between said second subchamber and said first subchamber to be reduced to a predetermined threshold amount wherein the magnetic biasing force moves said flexible diaphragm from said second position to said first position.

7. An intermittent suction device as described in claim 6 wherein said means to cause the pressure differential between said second subchamber and said first subchamber to be reduced comprises means to reduce the pressure in said second subchamber to below atmospheric pressure.

8. An intermittent suction device adapted to be connected to a source of vacuum for alternately supplying timed vacuum and atmospheric pressure to a patient for removing fluids from the patient, said device comprising a housing having a chamber, said chamber having a flexible diaphragm separating said chamber into first and second subchambers, said first subchamber having an inlet adapted to be connected to the source of vacuum and an outlet for applying vacuum and atmospheric pressure to the patient, said flexible diaphragm having a first position wherein said outlet is open to communicate vacuum from the vacuum source to said outlet through said first subchamber and a second position wherein said flexible diaphragm closes said outlet to prevent communication of vacuum between said inlet and said outlet, valve means operable by said flexible diaphragm to allow atmospheric pressure to communicate with said outlet when said flexible diaphragm moves to said second position, said diaphragm being susceptible to magnetic forces, magnetic force means biasing said flexible diaphragm to said first position and control means to control the differential pressure between said first and second subchambers to move said diaphragm between said first and second positions.

9. An intermittent suction device as described in claim 8 wherein said valve means comprises a port communicating atmospheric pressure to said outlet, a movable valve member normally closing said port, said movable valve member having a valve stem projecting into said first subchamber, wherein said flexible diaphragm engages and moves said valve stem to open said port when said flexible diaphragm moves to its second position.

10. An intermittent suction device as described in claim 8 wherein said valve means comprises a passageway communicating atmospheric pressure to said inlet, a seat closing said passageway, said seat having an opening therethrough, and a valve magnet within said housing and located adjacent said seat opposite said flexible diaphragm, wherein the polarity of said valve magnet attracts said valve magnet toward said flexible diaphragm to close said opening when said flexible diaphragm is in its first position.

11. An intermittent suction device as described in claim 8 wherein said control means comprises means to create a higher pressure in said second subchamber to create a differential pressure between said first and second subchambers sufficient to overcome the magnetic biasing force to move said flexible diaphragm from said first position to said second position.

12. An intermittent suction device as described in claim 8 wherein said control means comprises means to cause the pressure differential between said second subchamber and said first subchamber to be reduced to a predetermined threshold amount wherein the magnetic biasing force moves said flexible diaphragm from said second position to said first position.

13. An intermittent suction device as described in claim 8 wherein said flexible diaphragm includes a permanent magnet.

14. An intermittent suction device as described in claim 13 wherein said flexible diaphragm closes said outlet when said permanent magnet attracts a magnetically operable valve.

15. An intermittent suction device as described in claim 9 wherein said flexible diaphragm is comprised of a magnetically polarized material.

16. An intermittent suction device for supplying a timed vacuum to a patient from a vacuum source for removing fluids from the patient, said device comprising a housing having a chamber, said chamber having a flexible diaphragm separating said chamber into a first and a second subchamber, said first subchamber having an inlet connected to the source of vacuum and an outlet for applying vacuum from the source to the patient, a first conduit connected to the source of vacuum and having a valve adapted to be opened and closed, a restrictor in said conduit located between said valve and the source of vacuum and a second conduit communicating with said second subchamber and connected to said first conduit at a point intermediate said restrictor and said valve, said flexible diaphragm having a first position wherein vacuum communicates between said inlet and said outlet, and a second position wherein said flexible diaphragm blocks communication of vacuum between said inlet and said outlet, said diaphragm being susceptible to magnetic forces, magnetic force means biasing said flexible diaphragm to said first position and means to open and close said valve at timed intervals to control the differential pressure between said first and second subchambers to move said flexible diaphragm between said first and second positions.

17. An intermittent suction device as defined in claim 16 wherein said valve comprises a housing having a chamber, said chamber having a magnetically susceptible diaphragm separating said chamber into a first and a second subchamber, said diaphragm having a first position wherein said second conduit is open and a second position wherein said second conduit is closed, magnet means biasing said diaphragm to said first position, and means to control the differential pressures between said first and second subchambers to move said diaphragm between said first and second positions.

18. An intermittent suction device as defined in claim 16 wherein said magnetic biasing means to bias both of said diaphragms comprises a magnet located intermediate said diaphragms.

19. An intermittent suction device as defined in claim 18 wherein said means to control the differential pressures between said first and second subchambers includes a flow path between said first and second subchamber including a restrictor and a compliance chamber.

20. An intermittent suction device as defined in claim 19 wherein said restrictor is a variable restrictor.

21. An intermittent suction device for supplying a timed vacuum to a patient from a source of vacuum for removing fluids from the patient, said device comprising a housing having a first chamber, said first chamber having first and second flexible diaphragms dividing said first chamber into first and second subchambers, said first subchamber of said first chamber having an inlet connectible to the source of vacuum and an outlet for applying vacuum from the vacuum source to the patient, said first diaphragm having a first position wherein said outlet is open to communicate vacuum from from said inlet to said outlet and a second position wherein said first flexible diaphragm closes said outlet to prevent communication of vacuum between said inlet and said outlet, magnetic force means biasing said first diaphragm toward it's first position, means to control the differential pressure between said first and second subchambers of said first chamber to move said first flexible diaphragm between said first and second positions at predetermined timed intervals, said means comprising a second chamber within said housing, said second chamber having a flexible diaphragm dividing said second chamber into first and second subchambers, said second chamber having a vacuum inlet port, a passage for connecting said vacuum inlet port to the source of vacuum, said passage containing a restrictor having a known resistance, said second diaphragm having a first position wherein said vacuum inlet is open to allow vacuum to be applied to said second subchamber of said second chamber and a second position wherein said second flexible diaphragm closes said vacuum ports magnetic force means biasing said second diaphragm towards it's first position, and means to control the differential pressure between said first and second subchambers of said second chamber to move said second flexible diaphragm between it's first and second positions at timed intervals, said movement of said second diaphragm affecting the movement of said first diaphragm.

22. An intermittent suction device as defined in claim 21 wherein said restrictor is a variable restrictor.

23. An intermittent suction device as defined in claim 22 wherein said means to control the differential pressure between said first and second subchambers of said second chamber includes a flow path between said first and second subchambers including a compliance chamber having a known volume and a restrictor having a predetermined resistance to flow.

24. An intermittent suction device as defined in claim 22 wherein said magnetic biasing means acting upon said first and second diaphragms comprises a permanent magnet contained within said housing and located between said first and second diaphragms.

* * * * *